(12) United States Patent
Martin et al.

(10) Patent No.: US 6,335,161 B1
(45) Date of Patent: Jan. 1, 2002

(54) RELEASE OF INTRACELLULAR MATERIAL AND THE PRODUCTION THEREFROM OF SINGLE STRANDED NUCLEIC ACID

(75) Inventors: Sophie E.V. Martin; Karin Bergmann, both of Cambridge; Denise V. Pollard-Knight, London, all of (GB)

(73) Assignee: Scientific Generics Limited, Cambridge (GB)

( * ) Notice: Subject to any disclaimer, the term of this patent is extended or adjusted under 35 U.S.C. 154(b) by 0 days.

(21) Appl. No.: 09/030,028

(22) Filed: Feb. 25, 1998

Related U.S. Application Data

(63) Continuation of application No. PCT/GB95/02024, filed on Aug. 25, 1995.

(51) Int. Cl.[7] .............................. C12Q 1/68; C12P 19/34; G01N 33/48
(52) U.S. Cl. ................ 435/6; 435/91.2; 436/94; 935/78; 935/16
(58) Field of Search .................. 435/6, 91.2; 436/94; 935/78, 16

(56) References Cited

U.S. PATENT DOCUMENTS 5,312,813 A   5/1994  Costerton et al. .............. 514/29
5,527,670 A * 6/1996  Stanley ............................ 435/6

FOREIGN PATENT DOCUMENTS

| GB | 1481480 | 7/1977 | |
| GB | 2247889 A | 3/1992 | ............ C07H/21/04 |
| WO | 88/02777 | 4/1988 | ............ C12N/13/00 |
| WO | 92/04470 | 3/1992 | ............ C12Q/1/68 |
| WO | 93/15224 | 8/1993 | ............ C12Q/1/68 |
| WO | 95/25177 | 9/1995 | ............ C12Q/1/68 |
| WO | 97/08293 | 3/1997 | ............ C12N/1/06 |

OTHER PUBLICATIONS

Heery, et al., "Curing of a plasmid from *E.coli* using high–voltage electroporation", Nucleic Acids Research, 1989, vol. 17, No. 2, pp. 10131.

Brodelius, et al., "Permeabilization of cultivated plant cells by electroporation for release in intracellulary stored secondary products,", Plant Cell Reports, 7:186–188.

* cited by examiner

*Primary Examiner*—Kenneth R. Horlick
*Assistant Examiner*—Joyce Tung
(74) *Attorney, Agent, or Firm*—Pillsbury Winthrop LLP

(57) ABSTRACT

Intracellular material is released from bacterial, yeast, plant, animal, insect or human cells by the application of a low voltage such as 1 to 10 V to a suspension containing the cells. The conditions may be selected such that DNA released from the cells is electrochemically denatured so as to be available for use in an amplification procedure.

6 Claims, 4 Drawing Sheets

| SAMPLE | TREATMENT |
|---|---|
| MW | MOLECULAR WEIGHT MARKER |
| CTRL | NEGATIVE CONTROL (LEFT IN BUFFER FOR THE WHOLE LENGTH OF THE EXPERIMENT) |
| 1 | 5 min, 2v, DC |
| 2 | 2 min, 2v, DC |
| 3 | 5 min, 8v, DC |
| 4 | 5 min, 4v, DC |
| 5 | 5 min, 2v, DC |
| 6 | 15 min, 4v, DC |
| 7 | 5 min, 1v, DC |

| SAMPLE | TREATMENT |
|---|---|
| 1 | 5 min, 8v, DC |
| 2 | 4 min, 8v, DC |
| 3 | 3 min, 8v, DC |
| 4 | 2 min, 8v, DC |
| 5 | 1 min, 8v, DC |
| CRTL | NEGATIVE CONTROL (LEFT IN BUFFER FOR THE WHOLE LENGTH OF THE EXPERIMENT) |

MW  1  2  3  4  5  CRTL 1 2 3 4 5 6 7 8 9 10 11 12  M

SEQUENCE LISTING

<160> NUMBER OF SEQ ID NOS: 2

<210> SEQ ID NO 1
<211> LENGTH: 21
<212> TYPE: DNA
<213> ORGANISM: Escherichia coli
<220> FEATURE:
<221> NAME/KEY: primer_bind
<222> LOCATION: (1)..(21)
<223> OTHER INFORMATION: PCR primer for amplifying 417 bp DNA fragment.

<400> SEQUENCE: 1
atgcgtccgg ccgtagagga t                                              21

<210> SEQ ID NO 2
<211> LENGTH: 16
<212> TYPE: DNA
<213> ORGANISM: Escherichia coli
<220> FEATURE:
<221> NAME/KEY: primer_bind
<222> LOCATION: (1)..(16)
<223> OTHER INFORMATION: PCR primer for amplifying 417 bp DNA fragment.

<400> SEQUENCE: 2
gtatcacgag gccctt                                                    16

RELEASE OF INTRACELLULAR MATERIAL AND THE PRODUCTION THEREFROM OF SINGLE STRANDED NUCLEIC ACID

This is a Continuation of International Appln. No. PCT/GB95/02024 filed Aug. 25, 1995 which designated the U.S.

FIELD OF THE INVENTION

The present invention relates to methods for producing release of intracellular material from cells.

Current methods for cell lysis and isolation of cellular material are laborious and time consuming and require a number of steps. For example, the preparation of DNA from bacteria requires a protocol of no fewer than ten individual steps. To produce effective cell lysis in gram negative bacteria, treatment with reagents such as EDTA and digestion with enzymes such as lysosyme and RNase are required. This is followed by cold shock, osmotic shock or boiling in order to release cellular material. Multiple steps are then necessary to harvest nucleic acids from the lysed preparation.

DESCRIPTION OF PRIOR ART

In the case genomic DNA isolation these are, following lysis of cells to release the DNA:
digestion of RNA and proteins with enzymes,
removal of contaminants, usually by solvent extraction,
and finally, dialysis or ethanol precipitation steps to give a clean preparation.

Plasmid extraction comprises cell lysis and selective precipitation of genomic DNA followed by the purification of plasmid DNA by gradient centrifugation or by ion-exchange chromatography. DNA extraction techniques currently in use include phenol-chloroform extraction and salting out methods for genomic DNA, and cesium chloride/ethidium bromide density gradients, and ion-exchange columns, for plasmid DNA. In addition kits are widely used for purification of DNA and DNA fragments which are based on the precipitation of DNA under chaotropic conditions. All of these techniques have their limitations. For example, density gradients and phenol/chloroform extraction are time consuming processes to use, taking up to 24 hours to perform. In addition, the copious use of phenol for these purposes is highly undesirable due to its toxic and caustic nature. Methods of isolating large fragments of DNA can result in DNA shearing.

It is known that electroporation using voltages in the kilovolt range can produce release of intracellular material through the permeablised cell membrane produced transiently in the electroporation process; see for instance Brodelius P. E. Funk C, Shillito R. D., Plant Cell Reports 7, 186 (1988) and Heery D. M., Powell R., Gannon, F., and Dunican L. K. Nuc. Acids Res. 17, 10131 (1989).

Electroporation involves the application of high voltages, typically in excess of 1 kV in pulses of short duration in the order of milliseconds. Generally, the field gradient between the electrodes across which the voltage is applied to a suspension containing the cells to be electro-porated will be in excess of 1 kV per cm. This requires sophisticated and expensive apparatus.

BRIEF SUMMARY OF THE INVENTION

It has now been found that it is possible to obtain release of intracellular material from cells by the application of voltages of a lower order of magnitude not previously thought to be capable of affecting cell membrane structure in such a way.

Accordingly, the present invention provides a method of producing release of intracellular material from cells comprising applying a voltage of not more than 50 volts to a suspension of said cells.

Preferably, the voltage is from 0.5 to 50 volts with a strong preference for voltages in the lower part of this range e.g. from 0.5 to 15 volts, most preferably from 1 to 10 volts.

The voltage may be a DC voltage or an AC voltage.

Unlike the practice in electroporation, the voltage may be applied continuously, subject to avoiding excess heating effects which may become a problem if the voltage is in excess of 15 volts. Preferably the voltage is applied for a period of at least 30 seconds, more preferably for at least 2 minutes, e.g. from 2 to 20 minutes. Preferably the voltage is applied continuously for a period as specified above, but this process may be repeated, e.g. by the application of voltage for repeated periods of several seconds to several minutes, e.g. 5 seconds to 10 minutes.

The electrodes by which the voltage is applied may preferably be spaced by 10 mm or less, e.g. 5 to 7 mm. However, it may be preferred to optimise the conditions for producing denaturation of double-stranded DNA released from the cells, in which case a smaller electrode spacing will be desirable. To accomplish denaturation of released DNA, preferably the voltage is applied to the suspension between closely spaced electrodes, preferably not spaced by more than 5 mm at their closest approach, e.g. by no more than 1.5 mm and most preferably by no more than 0.5 mm.

One of the electrodes may be constituted by a container of conductive material in which the sample being treated is contained.

The process may be conducted to produce cell lysis and to produce the release of intracellular materials including proteins and nucleic acids, including double stranded DNA, and other biomolecules. A process for producing denaturation of double-stranded nucleic acid utilising apparatus suitable for use in the present invention is described in Application PCT/GB95/00542. This process is itself an improvement on processes for electrochemical denaturation of double-stranded nucleic acid described in WO92/04470 and WO93/15224. As disclosed in those specifications, nucleic acid may be denatured reversibly by the application of an electrical voltage and such denaturation may be used as a step in a number of more complex tasks including hybridisation studies and nucleic acid amplification procedures such as PCR.

Nucleic acids released from cells by methods according to the present invention may be further processed according to the teachings of these specifications.

Accordingly, the present invention includes a method of producing single-stranded nucleic acid which comprises releasing double stranded nucleic acid from cells by applying a voltage of not more than 50 volts to a suspension of said cells with an electrode to release nucleic acid from said cells and denaturing the double-stranded nucleic acid by applying the same or a different voltage to said suspension with said electrodes to convert said double-stranded nucleic acid to single-stranded nucleic acid.

The range of voltage within which production of denaturation in this way is achievable will not be as wide as the range of voltage appropriate for producing cell lysis and accordingly it is preferred that in the denaturation stage, a voltage of from 0.5 to 3 volts is applied, more preferably from 1.5 to 2.5 volts, measured as a voltage difference between the electrodes.

As described in WO92/04470, one may employ a promoter compound such as methyl viologen to produce more rapid denaturation.

More generally, the promoter may be any inorganic or organic molecule which increases the rate or extent of denaturation of the double helix. It should be soluble in the chosen reaction medium. It preferably does not affect or interfere with DNA or other materials such as enzymes or oligonucleotide probes which may be present in the solution. Alternatively, the promoter may be immobilised to the electrode or included in material from which the electrode is constructed. It may be a water soluble compound of the bipyridyl series, especially a viologen such as methyl viologen or a salt thereof. Whilst the mechanism of operation of such promoters is not presently known with certainty, it is believed that the positively charged viologen molecules interact between the negatively charged nucleic acids such as DNA and the negatively charged cathode to reduce electrostatic repulsion therebetween and hence to promote the approach of the DNA to the electrodes surface where the electrical field is at its strongest. Accordingly, we prefer to employ as promoters compounds having spaced positively charged centres, e.g. bipolar positively charged compounds. Preferably the spacing between the positively charged centres is similar to the spacing between the positively charged centres in viologen. Other suitable viologens include ethyl viologen, isopropyl viologen and benzyl viologen.

Other promoters are described in WO93/15224, i.e. multivalent cations such as magnesium. Other multivalent cations which are effective and which can be used include lanthanum ($La^{3+}$). The cations as the promoter may include inorganic cations completed with inorganic or organic ligands, e.g. $Pt(NH_3)_6^{4+}$ and $Cr(NH_3)_6^{2+}$. The method of release of intracellular material of the present invention may be practised in the presence or in the absence of such a promoter, or in the presence or absence of a release promoting amount of any promoter.

At least in the denaturation stage it is preferred that where the electrodes most closely approach one another, one or both of the electrodes is pointed. Such an electrode may be provided with a single point or a plurality of points. There appears to be some inter-relationship between the ideal voltage applied and the shape of the electrode and it may be that there is a preferred or ideal field gradient at the point of the electrode which can be achieved by adjustment of the voltage to suit the sharpness of the part of the electrode at which the denaturation takes place. Optionally, one can conduct the denaturation using a constant current supply rather than a regulated voltage and this may serve to compensate for variations in the geometrical set-up of the electrodes between different denaturation operations.

Where a constant current regime is employed, it will generally be preferable to use a current of from 80 to 160 $\mu A$, e.g. about 100 to 125 $\mu A$.

Optionally, the process may be conducted using a three electrode system of the kind described in WO92/04470 but generally it is preferred that the volume of solution employed according to this invention is small e.g. 1 ml or less, preferably very small e.g. 100 $\mu l$ or less, e.g. about 25 $\mu l$ to 40 $\mu l$. When using very small reaction volumes of this kind, it will generally not be practical to use a three electrode system.

The processes e.g. of cell lysis and of denaturation may each be carried out at ambient temperatures or if desired at temperatures up to adjacent the pre-melting temperature of the nucleic acid. Each process may be carried out at a pH of from 3 to 10, conveniently about 7. Generally, more rapid denaturation is obtained at lower pH. For some purposes therefore a pH somewhat below neutral e.g. about pH 5.5 may be preferred. The cells may be suspended in an aqueous solution containing a buffer whose nature and ionic strength are such as not to interfere with the strand separation process.

Preferably, the solution contains a buffer at a concentration at least 10 mM e.g. about 25 mM. Optionally, the solution may contain further salts such as magnesium chloride and sodium chloride. Preferably, the method is conducted in a buffer of the kind used in PCR or in LCR procedures.

Preferably, therefore the ionic strength of the solution is above 20 mM, e.g. 25 to 50 mM.

The release of nucleic acid and the denaturing process according to the invention may be incorporated as steps in a number of more complex processes, e.g. procedures involving the analysis and/or the amplification of nucleic acid. Some examples of such processes are described below.

We have found that by virtue of the superior electrochemical cell design described in PCT/GB95/00542 it is possible to achieve denaturation within less than 3 minutes e.g. from 1 to 2 minutes or less even in the presence of materials such as PCR buffers.

This makes it possible to practise a process of repeated denaturation of double-stranded nucleic acid wherein the nucleic acid is denatured by a process as described above in which the voltage is applied as sequence of repeated pulses having a duration of up to 2 minutes, preferably up to only 1 minute. Between pulses, the voltage may be turned off or reversed for a period which is preferably equal to the period for which the voltage is applied. It is possible to employ pulses of considerably higher frequencies than described above, e.g. from 1 to 100 Hz. Depending upon the purpose for which the denaturation is being conducted, it may not be necessary to achieve any substantial amount of conversion of double-stranded to single-stranded nucleic acid in each denaturation cycle. It may be sufficient merely to initiate denaturation electrochemically. For instance, in an amplification procedure, if sufficient denaturation occurs to allow binding of a primer, the extension of the primer by nuclease may be relied upon to displace the unprimed strand of the original nucleic acid from its binding partner over the remainder of the length of the nucleic acid.

The invention further provides a process of amplifying a target sequence of nucleic acid comprising hybridisation, amplification and denaturation of nucleic acid wherein the nucleic acid is released from a cell as described above and said denaturation is conducted by subjecting a solution containing said nucleic acid to a voltage applied between electrodes for a period of up to 2 minutes under conditions such as to covert at least a portion of the nucleic acid to a wholly or partially single-stranded form in the solution. Preferably, the electrode configuration used in such a process is as described above. Preferably, the voltage is applied as a repeating pulse having a duration of up to 1 minute but preferably shorter, e.g. up to 0.1 minute or even much shorter, e.g. at 1 to 100 Hz.

Preferably, the amplification procedure is PCR or LCR.

Thus the present invention includes a process for replicating a nucleic acid which comprises: releasing double stranded nucleic acid from cells by a process as described above; separating the strands of a sample double-stranded nucleic acid in solution under the influence of an electrical voltage applied to the solution from an electrode; hybridising the separated strands of the nucleic acid with at least one oligonucleotide primer that hybridises with at least one of the strands of the denatured nucleic acid; synthesising an extension product of the or each primer which is sufficiently complementary to the respective strand of the nucleic acid to hybridise therewith; and separating the or each extension product from the nucleic acid strand with which it is hybridised to obtain the extension product.

The replication process may be a step in a 3SR or NASBA amplification procedure or a strand displacement assay.

In such a polymerase mediated replication procedure, e.g. a polymerase chain reaction procedure, it may not be necessary in all cases to carry out denaturation to the point of producing wholly single-stranded molecules of nucleic acid. It may be sufficient to produce a sufficient local and/or temporary weakening or separation of the double helix in the primer hybridisation site to allow the primer to bind to its target. Once the primer is in position on a first of the target strands, rehybridisation of the target strands in the primer region will be prevented and the other target strand may be progressively displaced by extension of the primer or by further temporary weakening or separation processes.

Preferably, the said replication process further comprises repeating the procedure defined above cyclicly, e.g. for more than 10 cycles, e.g. up to 20 or 30 cycles. In the amplification process the hybridisation step is preferably carried out using two primers which are complementary to different strands of the nucleic acid.

The denaturation to obtain the extension products as well as the original denaturing of the target nucleic acid is preferably carried out by applying to the solution of the nucleic acid the voltage from the electrodes.

The process may be a standard or classical PCR process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being amplified, under conditions such that for each different sequence being amplified an extension product of each primer is synthesised which is complementary to each nucleic acid strand, wherein said primers are selected so as to be substantially complementary to different strands of each specific sequence such that the extension product synthesised from one primer, when it is separated from its complement, can serve as a template for synthesis of the extension product of the other primer;

(b) separating the primer extension products from the templates on which they were synthesised to produce single-stranded molecules by applying the voltage from the electrode to the reaction mixture; and (c) treating the single-stranded molecules generated from step (b) with the primers of step (a) under conditions such that a primer extension product is synthesised using each of the single strands produced in step (b) as a template.

Alternatively, the process may be any variant of the classical or standard PCR process, e.g. the so-called "inverted" or "inverse" PCR process or the "anchored" PCR process.

The invention therefore includes the use of an amplification process as described above in which a primer is hybridised to a circular nucleic acid released from a cell as described and is extended to form a duplex which is denatured by the application of the denaturing voltage, the amplification process optionally being repeated through one or more additional cycles.

The process of the invention is applicable to the ligase chain reaction. Accordingly, the invention includes a process for amplifying a target nucleic acid comprising the steps of releasing the target nucleic acid from a cell as described followed by:

(a) providing nucleic acid of a sample as single-stranded nucleic acid;

(b) providing in the sample at least four nucleic acid probes, wherein:
   i) the first and second said probes are primary probes, and the third and fourth of said probes are secondary nucleic acid probes;
   ii) the first probe is a single strand capable of hybridising to a first segment of a primary strand of the target nucleic acid;
   iii) the second probe is a single strand capable of hybridising to a second segment of said primary strand of the target nucleic acid;
   iv) the 5' end of the first segment of said primary strand of the target is positioned relative to the 3' end of the second segment of said primary strand of the target to enable joining of the 3' end of the first probe of the 5' end of the second probe, when said probes are hybridised to said primary strand of said target nucleic acid;
   v) the third probe is capable of hybridising to the first probe; and
   vi) the fourth probe is capable of hybridising to the second probe; and (c)
   i) hybridising said probes with nucleic acid in said sample;
   ii) ligating hybridised probes to form reorganised fused probe sequences; and
   iii) denaturing DNA in said sample by applying a voltage to the reaction mixture.

The electrochemical DNA release and amplification technique can be used analytically to detect and analyse a very small sample of DNA e.g. a single copy gene in an animal cell or a single cell of a bacterium.

The temperature at which the process is carried out may be chosen to suit whichever enzyme is used. Thus where Taq is used as polymerase, a temperature of 55 to 68° C. is preferred. If Klenow polymerase is used, ambient temperature will be suitable. It may be desirable to employ known protein stabilisation techniques to avoid electrical damage to the polymerase, especially where a mesophyllic polymerase is used.

The invention includes a process for detecting the presence or absence of a predetermined nucleic acid sequence in a cell which comprises: releasing nucleic acid from the cell as described, denaturing released double-stranded nucleic acid by means of a voltage applied to the nucleic acid; hybridising the denatured nucleic acid with an oligonucleotide probe for the sequence; and determining whether the said hybridisation has occurred.

Thus, the invented process has application in DNA and RNA hybridisation where a specific gene sequence is to be identified e.g. specific to a particular organism or specific to a particular hereditary disease of which sickle cell anaemia is an example. To detect a specific sequence it is first necessary to prepare a sample of DNA, by the release of the DNA from a cell as described which is in native double-stranded form. It is then necessary to convert the double-stranded DNA to single-stranded form before a hybridisation step with a labelled nucleotide probe which has a complementary sequence to the DNA sample can take place. The process of the invention can be used for this purpose in a preferred manner by carrying out the following steps:

releasing DNA from a cell by the method described above;

denaturing the DNA by applying a voltage by means of an electrode configuration as described to the sample DNA with optionally a promoter in solution or bound to or part of the structure of the electrode;

hybridising the denatured DNA with a directly labelled or indirectly labelled nucleotide probe complementary to the sequence of interest; and determining whether the hybridisation has occurred, which determination may be by detecting the presence of the probe, the probe being directly radio-labelled, fluorescent labelled, chemiluminescent labelled or enzyme-labelled or being an indirectly labelled probe which carried biotin for example to which a labelled avidin or avidin type molecule can be bound later.

In a typical DNA probe assay it is customary to immobilise the sample DNA to a membrane surface which may be composed of neutral or charged nylon or nitrocellulose. The immobilisation is achieved by charge interactions or by baking the membrane containing DNA in an oven. The sample DNA can be heated to high temperature to ensure conversion to single-stranded form before binding to the membrane or it can be treated with alkali once on the membrane to ensure conversion to the single-stranded form. The disadvantages of such methods are:

heating to high temperature to create single-stranded DNA can cause damage to the sample DNA itself;

the use of alkali requires an additional step of neutralisation before hybridisation with the labelled probe can take place.

One improved method for carrying out DNA probe hybridisation assays is the so-called "sandwich" technique where a specific oligonucleotide is immobilised on a surface. The surface having the specific oligonucleotide thereon is then hybridised with a solution containing the target DNA in a single-stranded form, after which a second labelled oligonucleotide is then added which also hybridises to the target DNA. The surface is then washed to remove unbound labelled oligonucleotide, after which any label which has become bound to target DNA on the surface can be detected later.

This procedure can be simplified by using the cell lysis and denaturing process of the invention to denature the target DNA from double-stranded into the required single-stranded DNA which can hybridise to the immobilised oligonucleotide. The working electrode, counter-electrode and optionally a reference electrode and/or a promoter can be incorporated into a test surface or a well in which the DNA probe assay is to be carried out. The cell sample and oligonucleotide probes can then be added and the voltage applied to release and denature the DNA. The resulting single-stranded DNA is hybridised with the specific oligonucleotide immobilised on the surface after which the remaining stages of a sandwich assay care carried out. All the above steps can take place without a need for high temperatures or addition of alkali reagents as in the conventional process.

The release of the nucleic acids from the cell or cells and the denaturation of the nucleic acids may be conducted under similar conditions in which case there may be no clear division between the steps of cell release and denaturation. The nucleic acid may be denatured as it is released from the cells.

Other cell contents than nucleic acid may of course be released according to the methods of the invention and the release of such other materials may be utilised in various ways for instance, the release of specific proteins may be used as a step in an assay procedure in which such proteins are detected. RNA released may be detected in hybridisation assays or amplified, e.g. by 3SR or NASBA techniques. Generally, intracellular materials released by methods according to the invention may be utilised for all of the purposes for which such materials have been utilised when released by conventional cell lysis procedures.

BRIEF DESCRIPTION OF THE DRAWINGS

The invention will be further described and illustrated with reference to the accompanying drawings in which.

DETAILED DESCRIPTION OF THE INVENTION

Figure 1:
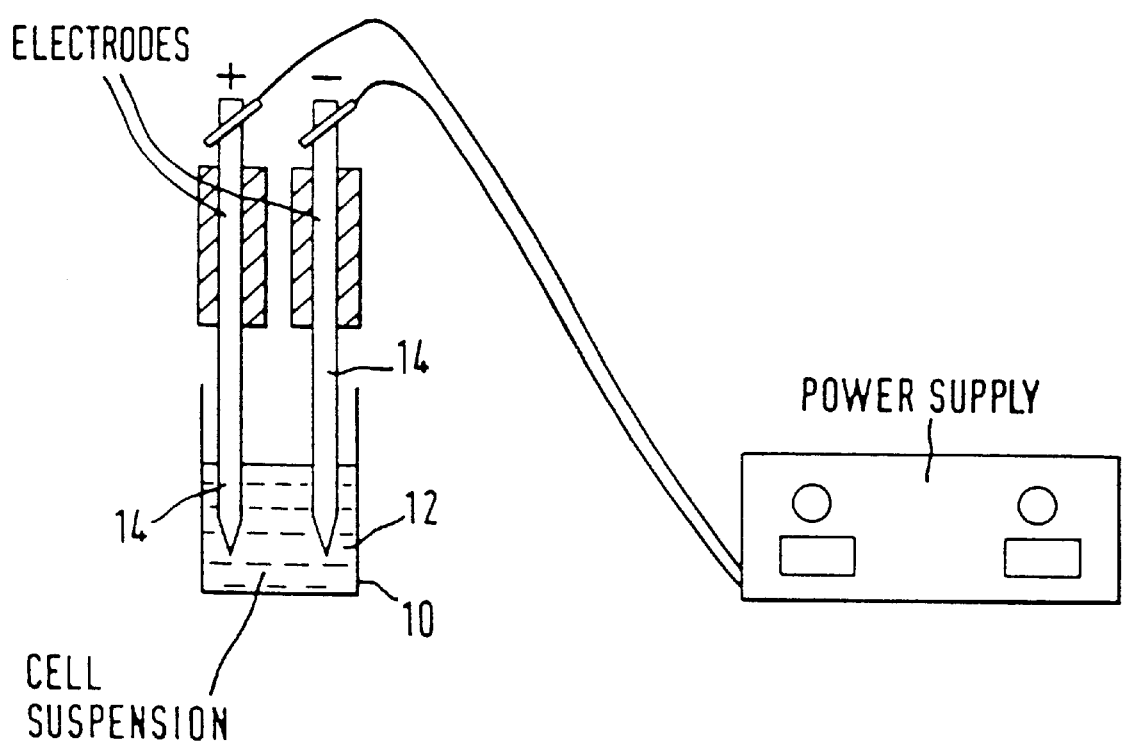
FIG. 1 is a cross-sectional view through an electrical cell for use in accordance with the invention.
Figure 2:
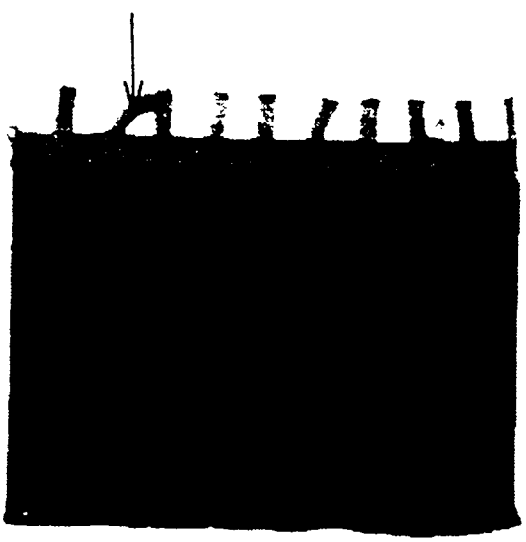
FIG. 2 is a gel produced in Example 1 showing release of protein from cells.

The cell shown in FIG. 1 comprises a glass container 10 having two electrodes 14 dipping into a cell suspension 12 therein. The electrodes 14 are parallel pointed carbon rods spaced by 5 to 8 mm and having a diameter above said tapered points of about 1 mm. A length of 5 to 15 mm of electrode is dipped into the suspension.

Figure 5:
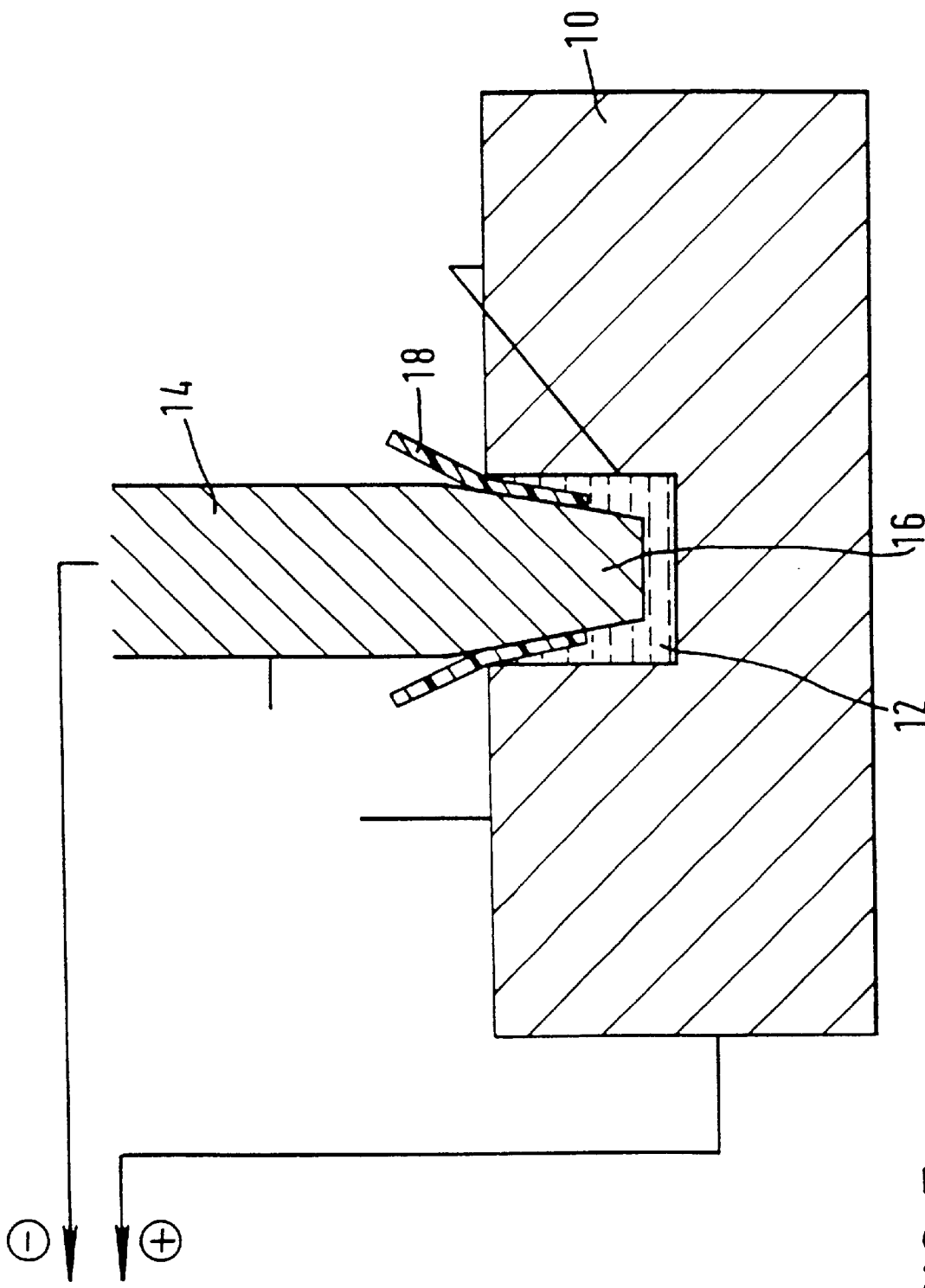
FIG. 5 is a cross-sectional view through an alternative electrical cell for use in the invention.

An alternative apparatus is shown in FIG. 5 where the cell illustrated comprises a graphite block 10, containing a 4 mm diameter well 12 on its upper surface, constituting a first electrode. A second electrode formed from a 2 mm diameter graphite rod 14 having a tapering end portion 16 is pressed into the well through an insulating collar of plastics material 18. The rod is adjusted down-wards in the well until it forms a short circuit and is then lifted back by as little as possible to open the circuit again. The capacity for liquid for the cell is approximately 25 $\mu$l. A DC voltage is applied to the apparatus with the well being made positive with respect to the rod by preferably 1.6 to 2.5 volts.

Although the rod electrode shown in FIG. 1 is blunt ended, it provides a sharp edge between its flat end and its tapering frustoconical surface. An optional alternative configuration is for the rod to be sharpened to a point. This may be achieved by using a conventional pencil sharpener. The resulting electrode may be further smoothed using a blade or abrasive. Using such a pointed electrode, the capacity for liquid of the well is increased to 40 $\mu$l.

Multiple processes according to the invention may be carried out simultaneously in apparatus containing a multiplicity of sample receiving wells each provided with a respective electrode pair, one electrode in each case optionally being the well itself. In a preferred form for such apparatus a block containing the wells has a liftable lid with electrodes depending therefrom into the wells. Each well may have a pair of electrodes on the lid in various possible electrode conformations such as parallel rods, parallel plates, optionally of mesh, or coaxial hollow cylinders, again optionally of mesh. Alternatively, single electrodes may be provided on the lid for each well and the block containing the wells may be conductive and may serve as a common second electrode. The block of wells may also contain respective electrodes for each well.

The lid may comprise a flat plate portion bearing the electrode or electrodes for each well and a separate backing member bearing electrical connections and circuitry which connects up the electrodes when the two parts are assembled. A single electrical supply to the unit may be split by said circuitry and supplied in a controlled manner to the electrodes such that each electrode is controlled, e.g. to a constant voltage or constant current. The plate portion carrying the electrode array may thereby be replaceable without replacement of the control circuitry and may be made disposable. The plate portion and the backing member may be aligned with one another on assembly by locating pins and apertures and may similarly be aligned with the block containing the wells, which also may be disposable.

The following example illustrate methods according to the invention.

EXAMPLE 1

Gram negative bacteria (*E. Coli* strain DH5αF (Gibco, BRL)) were grown overnight in Luria Bertani medium. The average cell density achieved was $1/10^9$ cells $ml^{-1}$. Harvested cells were washed in 1M Tris buffer, pH 8.0 and resuspended in ⅕ of the volume of the original culture. Two carbon electrodes were placed in the sample as shown in FIG. 1 and direct voltages of 2 to 8V were applied for 2 to 5 minutes. Positive control samples were boiled for 5 minutes. The cell debris was pelleted by centrifugation at 5000 rpm for 5 minutes and 20 μl of the supernatant was analysed by electrophoresis on a polyacrylamide gel, stained with Coomassie blue. The data demonstrate that applying a potential difference of 8 volts and 4 volts for 5 minutes (d.c.) resulted in protein release from the cell. Similar results are obtained using alternating voltage of 2 to 8V.

EXAMPLE 2

The same experimental conditions were used as in Example 1 above but using reduced electrocution times at 8 volts. This resulted in the release of protein from the cell even after only 1 minute.

EXAMPLE 3

In order to demonstrate DNA release and to increase the sensitivity of detection we assessed cell lysis by amplifying DNA using the polymerase chain reaction.

*Escherichia coli*, strain DH5αF (Gibco, BRL) were transformed with pBR322 (Sigma) and grown overnight in Luria Bertani medium containing 100 $\mu gml^{-1}$ ampicillin. The average cell density achieved was $1 \times 10^8$ cells $ml^{-1}$. Cells were harvested by centrifugation at 10000 rpm for five minutes and washed in PCR buffer (10 mM Tris, 50 mM KCl, 2.5 mM $MgCl_2$, pH 8.3). Cells were resuspended in PCR buffer at a concentration five times that of the original. Positive control samples were treated by boiling for 5 minutes.

Figure 3:
FIG. 3 is a gel produced in Example 2 showing release of protein from cells.
Figure 4:
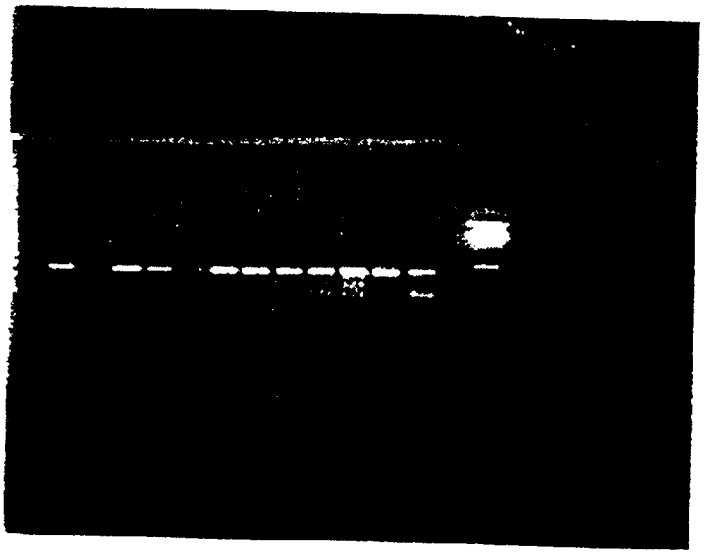
FIG. 4 is a gel produced in Example 3 showing PCR amplification of DNA released from cells.

Two carbon probe electrodes were placed into the sample and 4–8 V (d.c.) was applied (power supply; Thurlby 30V, 2A) for between 0.5 to 2 minutes. The cell debris was pelleted and supernatants were analysed by PCR. PCR conditions were as follows; 0.1 μl/ml of sample in PCR buffer (as above), 1 μM (each) of primers ATGCGTCCG-GCCGTAGAGGAT SEQ ID NO. 1 and GTATCACGAG-GCCCTT SEQ ID NO. 2, 200 μM of each of dATP, dCTP, dGTP, dTTP, 5U/ml AmpliTaq DNA polymerase (Perkin Elmer). All reagent concentrations are given as the final concentration in a reaction volume made up with PCR buffer (as above). Amplified DNA was analysed on agarose gels stained with ethidium bromide. An amplified DNA fragment of the expected molecular weight (417 bp) was observed in samples which had been subjected to the shortest test time of 30 seconds (see FIG. 3). The density of the bands indicated that cell lysis, induced by an applied voltage, released DNA in excess of the background (non-lysed cells control) level.

What is claimed is:

1. A method of producing single stranded nucleic acid which comprises releasing double stranded nucleic acid from cells by applying a voltage of not more than 50 volts to a suspension of said cells with an electrode to release nucleic acid from said cells and denaturing the double stranded nucleic acid by applying the same or a different voltage to said suspension with said electrode to convert said double stranded nucleic acid to single stranded nucleic acid.

2. The method of claim 1, wherein to produce said denaturation, a voltage of from 0.5 to 3 volts is applied.

3. The method of claim 1, wherein to produce said denaturation, a voltage of from 1.5 to 2.5 volts is applied.

4. The method of claim 1, wherein the denaturation is conducted in the presence of an agent which assists denaturation.

5. The method of claim 4, wherein said agent is methyl viologen or a salt thereof or is a multivalent inorganic cation.

6. A process for detecting the presence or absence of a predetermined nucleic acid sequence in a cell which comprises: releasing nucleic acid from the cell by a method comprising applying a voltage of not more than 50 volts to a suspension containing said cell or cells, denaturing released double-stranded nucleic acid by means of a voltage applied to the nucleic acid; subjecting the denatured nucleic acid to hybridisation with an oligonucleotide probe for the predetermined nucleic acid sequence; and determining whether the said hybridisation has occurred so as to detect the presence or absence of said predetermined nucleic acid sequence.

* * * * *